United States Patent [19]

Nichols et al.

[11] Patent Number: 5,747,017

[45] Date of Patent: May 5, 1998

[54] LIP COSMETIC

[75] Inventors: Rosemarie Nichols, Manhattan Beach; Martin J. Weisman, Canoga Park, both of Calif.

[73] Assignee: Lip-Ink International, El Segundo, Calif.

[21] Appl. No.: 440,780

[22] Filed: May 15, 1995

[51] Int. Cl.$^6$ ............................... A61K 7/04; A61K 9/14
[52] U.S. Cl. ............... 424/61; 424/401; 424/486; 424/487; 424/498; 424/495
[58] Field of Search ................... 424/61, 64, 47, 424/401

[56] References Cited

U.S. PATENT DOCUMENTS

| | | | |
|---|---|---|---|
| 2,230,063 | 1/1941 | Klimist | 167/85 |
| 3,646,214 | 2/1972 | Katz | 424/362 |
| 4,192,861 | 3/1980 | Micchelli et al. | 424/47 |
| 4,315,910 | 2/1982 | Nowak, Jr. et al. | 424/47 |
| 4,534,961 | 8/1985 | Liff | 424/63 |
| 4,904,698 | 2/1990 | Adkins, Jr. et al. | 514/642 |
| 4,935,228 | 6/1990 | Finkenaur et al. | 424/64 |
| 5,238,678 | 8/1993 | Shiozawa et al. | 424/63 |
| 5,505,937 | 4/1996 | Castrogiovanni et al. | 424/64 |

FOREIGN PATENT DOCUMENTS

| | | |
|---|---|---|
| 0005922 | 5/1979 | European Pat. Off. . |
| 2638636 | 11/1988 | France . |
| WO86/02001 | 4/1986 | WIPO . |
| WO92/19215 | 11/1992 | WIPO . |

OTHER PUBLICATIONS

"Harry's Cosmeticology", pp. 332–333 (Coloured Make–up Preparations), 7th Ed., Chemical Publishing Co. 1982.
AMPHOMER—Polymer for Hard Holding Hair Fixative Formulations:, National Starch and Chemical Company, Specialty Polymers.

*Primary Examiner*—Thurman K. Page
*Assistant Examiner*—Sharon Howard
*Attorney, Agent, or Firm*—Knobbe Martens Olson & Bear, LLP

[57] ABSTRACT

An improved lip cosmetic employing a coloring agent and a plasticizer in a volatile solvent includes a film-forming agent which preferably has as components an AMPHOMER and ethyl cellulose, as well as a cosmetic pigment. The lip cosmetic of the invention includes between about one and about ten parts of an alcohol soluble and water insoluble resin, between about one and about ten parts ethyl cellulose, between about one and about ten parts of a dispersion of cosmetic pigments in castor oil, and between about seventy and about ninety-five parts of an organic solvent. The resultant lip cosmetic is water insoluble and has a staying power far greater than that of conventional lipstick. The novel lip cosmetic will not smear and come off on beverage receptacles, fabrics, or the human skin once it drys. The finish is so sheer that the lip cosmetic can be applied in at least three successive layers without caking up or cracking. Once applied in this fashion, while allowing each layer to dry between each successive application, a person can shower, swim, smoke, kiss, and imbibe beverages without leaving stains from the lip cosmetic on coffee cups, cheeks, or collars.

7 Claims, No Drawings

LIP COSMETIC

BACKGROUND OF THE INVENTION

1. Field of the Invention

The present invention relates to a lip cosmetic which is an advantageous alternative to lipstick.

2. Description of the Prior Art

For many years lipstick has been utilized as a cosmetic preparation for heightening or altering the color of the lips. Conventional lipstick is formed by a cosmetic coloring in a wax carrier. Although lipstick has many disadvantages there has thus far been no suitable alternative.

The lipsticks which have heretofore been available have the marked disadvantage of being readily transferrable from a person's lips to other objects. Lipstick smears and rubs off while swimming, smoking, kissing, or by any other contact of the lips with articles such as coffee cups, tea cups, napkins, and clothing. This leads to the loss of the lipstick application when drinking beverages, when swimming, and even when in engaging in none of these activities due simply to licking the lips. Thus, while lipstick is normally initially applied in a relatively even application across the externally exposed areas of the lips, the application of lipstick will readily dissipate and assumes a nonuniform coverage. The greatest loss of the lipstick application is typically near the portions of the lips closest to a person's mouth. As a consequence, it is necessary to frequently reapply layers of lipstick in order to maintain a uniform coverage of a lipstick application on a person's lips. This frequent necessity for reapplication aggravates a further disadvantage of conventional lipstick.

Lipstick has the additional disadvantage of being susceptible to cracking and caking. This disadvantage is particularly pronounced when several layers of lipstick have been applied to attempt to replenish a lipstick application that has been lost due to transfer to other articles. As a consequence, the frequent reapplication of lipstick results in perceptible cracking and caking of the lipstick covering a person's lips. Caking and cracking of a lipstick application detracts from the natural appearance of the lips and is aesthetically undesirable.

Attempts have been made over the years to provide alternative lip cosmetics which do not entail the disadvantages of lipstick. For example, U.S. Pat. No. 2,230,063 describes a liquid lip rouge preparation which employs a combination of ethyl cellulose and wax-free shellac as film-forming materials. However, shellac does tend to crack. Heretofore, no suitable alternative to lipstick has been found.

SUMMARY OF THE INVENTION

The present invention is an innovative new alternative to lipstick. The lip cosmetic of the present invention does not take the form of a gooey stick, but rather is a unique, smear-proof and waterproof liquid that dries quickly to an extremely sheer, soft finish that feels remarkably like bare skin.

The lip cosmetic of the present invention is both smear-proof and waterproof. It will not streak, smear, or rub off while swimming, smoking, or kissing. Use of the lip cosmetic of the present invention avoids the disadvantages of stains on coffee cups, cheeks, and collars. The lip cosmetic of the present invention has twice the staying power of lipsticks which purport to be waterproof or kiss-proof.

The lip cosmetic of the present invention has further advantages in that it won't stick to dental work or braces. It can also be used on hair or eyebrows as well as to cover any bald areas on the head. It can be used to cover scars or tattoos anywhere on the body.

The present invention provides a perfect lip cosmetic for busy professional women. It is highly advantageous for wear at weddings, parties, for use at the beach, for use while skiing, and for wear during all active sports. The lip cosmetic of the invention is extremely attractive and can be worn at important dinner dates, as well as during informal events. The wearer can even sleep or shower while wearing the lip cosmetic, since it will not fade or smear under such circumstances.

In one broad aspect the invention may be considered to be a lip cosmetic comprising between about one and about ten parts of an alcohol soluble and water insoluble resin, between about one and about ten parts ethyl cellulose, between about one and about ten parts of a cosmetic pigment, and between about seventy and about ninety-five parts of an organic solvent. All parts are by weight and the preferred solvent is denatured alcohol.

In another broad aspect the invention may be considered to be an improvement in a lip cosmetic employing a coloring agent and a plasticizer in a volatile solvent. The improvement is comprised of at least one film-forming agent present in an amount of at least about one percent wherein the film-forming agent is selected from the group consisting of: AMPHOMER (copolymers of N-tert-octylacrylamide, methyl methacrylate, hydroxprolyl methacrylate, acrylic acid and/or t-butyl aminoethyl methacrylate), AMPHOMER LOVOCRYL-47 (an octylacrylamide/acrylate/butylaminoethyl methacrylate copolymer), Carboset, JONCRYL (styrene/acrylate copolymer), QUADAMER (terpolymers of alkyl acrylamide, acrylamide or methacrylamide, N-vinyl pyrrolidone, and acrylic or methacrylic acid), GANTREZ (copolymers of vinyl methyl ether and monoalkyl esters of maleic anhydride, and polyvinyl acetate copolymers.

In yet another broad aspect the invention may be considered to be an improvement in a lip cosmetic employing a pigment and a film-forming agent in an organic solvent carrier. According to the improvement of the invention the film-forming agent includes an alcohol soluble and a water insoluble substance present in an amount of at least about one percent and selected from the group consisting of AMPHOMER, AMPHOMER LOVOCRYL-47, Carboset, JONCRYL, QUADAMER, GANTREZ, and polyvinyl acetate copolymers.

The critical component of the invention is the alcohol soluble and water insoluble resin. A number of different resins of the type may be employed in formulating the lip cosmetic of the invention. The alcohol soluble, water insoluble resin may be selected from the group consisting of octylacrylamides, acrylates, butylaminoethyl methacrylate copolymers, and polyvinyl acetate copolymers. The alcohol soluble, water insoluble resin or mixture of resins serves as a vital component of the film-forming agent. This film-forming agent may be selected from the group consisting of: AMPHOMER, AMPHOMER LOVOCRYL-47, Carboset, JONCRYL, QUADAMER, GANTREZ, and polyvinyl acetate copolymers. However, while any of these different substances can be utilized in the formulation of the lip cosmetic of the invention, the alcohol soluble, water insoluble resin that serves as the film-forming agent preferably includes an AMPHOMER component. In the preferred formulation the film-forming agent is preferably comprised of an AMPHOMER and ethyl cellulose.

Amphomer is a trademark under which copolymers of N-tert-octylacrylamide, methyl methacrylate, hydroxypropyl methacrylate, acrylic acid and t-butyl aminoethyl methacrylate are sold. GANTREZ is a trademark under which copolymers of vinyl methyl ether and mono-alkyl esters of maleic anhydride are sold by GAF. QUADAMER is a trademark under which terpolymers of alkyl acrylamide, acrylamide or methacrylamide, N-vinyl pyrrolidone, and acrylic or methacrylic acid are sold by American Cyanamid. The preferred film-forming agent is the commercially available Amphomer sold as LV-71 by National Starch and Chemical Company, Specialty Polymers, having an address of 10 Finderne Avenue, P.O. Box 6500, Bridgewater, N.J. 08807-3300.

The amphoteric acrylic resin forming the chemicals sold in the trade as Amphomer has previously been utilized as a fixative in hair spray as described, for example, in U.S. Pat. Nos 4,192,861 and 4,315,910. However, applicant has discovered that this substance can also serve as the preferred form of the critical ingredient of a lip cosmetic which forms a clear, colorless film on the lips and which has a staying power far greater than that of conventional lipsticks.

The AMPHOMER utilized in the lip cosmetic of the invention functions as a transparent sealer. It binds and seals the lip cosmetic to the lips in a clear, sheer film which does not crack or cake. The film-forming agent in the lip cosmetic composition is what makes the product so long lasting.

The AMPHOMER is an amphoteric acrylic resin. Its official Cosmetic Toiletries and Fragrances Association (CTFA) product designation is Octylacrylamide/Acrylates/Butylaminoethyl Methacrylate Copolymer. AMPHOMER is carboxylated at regular intervals along its molecular chain. In its undissolved form it is a fine white free-flowing powder. It has an intrinsic viscosity of 0.40 in ethanol at 25 degrees Centigrade. It contains about 3 percent volatiles and has an acidity of 2.05 me/gram.

The lip cosmetic of the invention contains no waxes or petroleum products. Waxes can smear while petroleum products can burn or dry the lips. The lip cosmetic of the invention is so sheer that a wearer can layer on at least three different layers without any danger of the product caking up on the lips. Indeed, the different layers of the lip cosmetic of the invention can be applied in different colors to achieve a unique, aesthetic effect.

Also, a different number of layers of the lip cosmetic can be applied to produce different aesthetic appearances. A single layer of the preferred embodiment of the lip cosmetic of the invention dries to a sheer finish. If a second layer of the lip cosmetic is applied over the first, a medium matte finish is achieved. By applying a third layer a wearer achieves a full cover matte finish. Even with use of multiple layers, however, the lip cosmetic of the invention will not cake, crack, or smear.

The lip cosmetic of the invention can be formulated in any number of different colors by varying the color of the pigment employed. The lip cosmetic of the invention is in a liquid form when applied and the colors can be used individually or mixed by layering to create an unlimited array of custom, personalized colors. Each layer takes about twenty seconds to dry from the time of application.

In addition to its basic components, the cosmetic of the invention may include other substances to achieve certain effects. For example, the lip cosmetic may be formulated with at least about one part of a dimethicone component to achieve a gloss or satin effect. Although the lip cosmetic formulated in this manner looks and feels viscid or sticky, it will not come off but will stay on the lips despite extended wear and exposure to moisture.

The lip cosmetic may also be formulated as a lip liner by utilizing a higher concentration of cosmetic dyes or colorings in the formulation. When formulated in this manner the lip cosmetic may be utilized to outline the lips in the same or a different color as the basic application.

The lip cosmetic of the invention provides natural sun protection and keeps the lips from chapping, indoors or outdoors, in both cold and hot weather. It will not stick to teeth or dental braces. Unlike a user wearing lipstick, an individual wearing the lip cosmetic of the present invention can actually brush and floss after meals without smearing the lip cosmetic or reducing the thickness of its lip coating, and without having to reapply the lip covering.

The lip cosmetic of the invention is organic and hypoallergenic. Unless a fragrance is added, it is also odor free and contains no petroleum products.

The lip cosmetic of the invention enhances the beauty of the wearer without surgery by filling in the inner lips where conventional lipstick will not stay. The lip cosmetic of the invention is extremely sheer and is not gooey like conventional lipstick. Even after three or more layers of the lip cosmetic of the invention are applied, the lips still feel bare and have a perfect matte finish.

The lip cosmetic of the invention is not at all viscous, and can even be poured from a container. Its sheer consistency allows it to be applied with a fine tip applicator so that it can be applied with the precision of a makeup artist.

The AMPHOMER utilized in the lip cosmetic of the invention functions as a transparent sealer. It binds and seals the lip cosmetic to the lips in a clear, sheer film which does not crack or cake. The film-forming agent in the lip cosmetic composition is what makes the product so long lasting.

The lip cosmetic of the invention will not come off with petroleum jelly or cleansing cream. Due to its permanence care must be taken not to spill the cosmetic of the invention in liquid form onto clothing or other fabrics. However, if the lip cosmetic is accidentally spilled onto carpeting or clothing, it can be readily removed with only isopropyl alcohol, provided that cleanup is undertaken promptly.

To use the lip cosmetic of the invention, it is recommended that the lip area be cleaned thoroughly with denatured ethyl alcohol such as SDA 40B-190 or soap and water. A bottle of the lip cosmetic containing a small mixing ball should be shaken for four to five times until the mixing ball moves freely within the bottle.

The lip cosmetic of the invention is then applied generously in liquid form to dry, clean lips. It is recommended that three consecutive layers be applied at a time for full day time coverage. The lip cosmetic can be applied with a stick or brush applicator and should be applied across the lips in a single direction only. When applying the lip cosmetic the wearer should keep in mind the freedom of creating fuller lips by filling in the inner lips where regular lipstick does not stay. Approximately twenty seconds should be allowed to elapse between consecutive coats in order to allow the immediately preceding coat to dry. During this time the lips should be kept apart and not blotted. For best results after the application of the lip cosmetic of the invention, the wearer should refrain from eating, drinking, or smoking for at least five minutes.

With the application of the lip cosmetic the wearer's lips will tingle at first. This can be taken as a sign that the product is taking effect. This tingling sensation diminishes or goes away entirely with repeated usage, because the sealing effect of the product actually helps to eliminate the mild but ever present chapping common to most lips.

The tingling sensation which is sometimes present may be avoided by applying at first a thin layer of the lip cosmetic containing dimethicone. Subsequent layers of the same or a different formulation of the lip cosmetic may be applied to achieve the desired degree of sheer or matte finish.

The bottle containing the lip cosmetic of the invention should be kept closed after each use. With daily use a one quarter ounce bottle should last approximately two months.

As previously noted, the organic solvent or carrier employed is preferably denatured alcohol, sometimes termed ethyl alcohol or ethanol. Other organic solvents which may be employed instead of or in addition to denatured alcohol include stearyl alcohol, cetyl alcohol, cetearyl-cetostearyl alcohol, SDA alcohol, methyl alcohol, isopropyl alcohol, isostearyl alcohol, laurel alcohol, myristyl alcohol, behenyl alcohol, synthetic alcohol, and C18–40 alcohol. Other organic solvents which may be employed include higher fatty-acids which are immiscible in water. These include lauric acid, myristic acid, stearic acid, palmitic acid, behenic acid, and lanolin fatty acid. Lanolin and triterpene may also be employed in the organic solvent.

Depending upon the concentration of the other components, the organic solvent, which is preferably SDA 40B 190 denatured alcohol, is preferably present to the extent of between about thirty and ninety-five percent. Within this range a concentration of eighty to eighty-five percent organic solvent will normally be utilized.

The pigments which are employed to provide the coloring to the lip cosmetic are normally provided as dispersions in castor oil. The pigment and castor oil are preferably present in the lip cosmetic of the invention in an aggregate amount of between about one percent and about ten percent. Pigments of this type are standardized in the cosmetic industry and are identified in that industry by FD&C designations, D&C designations, and natural color designations that are compatible with alcohol solutions. The preferred pigments that are employed include D&C Red No. 6, Barium Lake, D&C Red No. 7 Calcium Lake, D&C Orange No. 5, D&C Red No. 27, FD&C Yellow No. 5, FD&C Blue No. 1, Soloron Silver, Timiron Super Violet, and others. The D&C lake colors are all made with aluminum, calcium, barium, potassium, strontium, or zirconium.

Other pigments which may be employed include those of dye or coal tar origin and chemical compounds used as pigments. Inorganic colors such as iron oxides may be utilized. White pigments may be formed of titanium dioxide, zinc oxide, mica, or pearls. Pigments formed of nitro dyes may be utilized if desired. These dyes contain one atom of nitrogen and two of oxygen. However, only a few nitro dyes are certified by the FD&C or D&C because nitro dyes can be absorbed through the skin, and some are toxic. However, D&C Yellow No. 5 is one acceptable nitro dye which can be used as a component of the pigment of the invention.

Azo pigments may also be utilized. These pigments are characterized by the presence of the azo bond, and monoazo pigments include the greatest number of pigments within this group.

Another group of suitable pigments is the triphenyl-methane group. FD&C Blue No. 1 is the most popular dye of the group and is widely used in the cosmetic industry. Xanthene pigments may also be utilized. This group of pigments includes Berry brilliant, which is widely used in lipstick colors, as well as D&C orange.

Certain of the quinoline dyes are also suitable for use as pigments. There are only two certified cosmetic colors in this category, namely D&C Yellow Nos. 10 and 11. These are bright greenish yellow colors.

The anthraquinone dyes are also suitable for use in formulating the pigment required by the lip cosmetic of the invention. These dyes are widely used in cosmetics because they are not affected by light. D&C Violet No. 2 is one example of such a dye suitable for use in the invention.

Indigo dyes are also suitable for use and have been used in cosmetics for many years. D&C Blue No. 6 is one example of a suitable indigo dye.

Pigments of vegetable, animal, or mineral origin may also be utilized according to the invention. One suitable pigment of animal origin is cochineal extract. Natural colors and vegetable compound pigments which may be utilized include alkanet, annatto, carotene, chlorophyll saffron and tumeric, beet juice powder, carmine, alkanet root, carmel, grape skin extract, beta carotene, and henna. Hydroxyascetone and indelible dyes may also be utilized in formulating the pigment in the lip cosmetic of the invention.

The preferred embodiments of the lip cosmetic of the invention employ pigments of coloring dispersed in castor oil. This dispersion is present to the extent of between one percent and ten percent of the formulation. The degree of concentration of the pigments in castor oil determines the shade of the coloring. Normally a concentration of between seven and nine percent pigments in castor oil, in the aggregate, is employed in formulating the lip cosmetic. The castor oil acts like a plasticizer and also makes the film formed more flexible.

The alcohol soluble, water insoluble resin which is employed is the critical component that provides the lip cosmetic of the invention with its numerous advantages over lipstick. While Amphomer is preferably utilized as the requisite alcohol soluble, water insoluble resin, other plasticizers, such as castor oil are also employed in the preferred formulations.

The preferred formulation of the lip cosmetic of the invention includes between one and ten percent Amphomer and one to ten percent of ethyl cellulose as the film-forming agent. Within this range between four and six percent of the Amphomer and three to four percent ethyl cellulose are preferably employed.

In addition to the basic components required to create an effective lip coating, the lip cosmetic of the invention may include other components as well. For example, it may include a dimethicone component, such as dimethicone-dimethicone copolyol, methyl silicone, or other dimethicones to enhance the shine of the lip cosmetic. For example, the topical application of Dow Corning Silicone 200 fluid 100–1000 centistokes creates a product of enhanced shininess without breaking down any of the attributes of the waterproof and smearproof properties of the lip cosmetic.

The lip cosmetic of the invention may also employ humactants, such as glycerin or propylene glycol, to keep the lip coating more moist. Flavorings, such as methyl sucrose, and fragrances, absolutes, extracts, and aromatics may also be included in the formulation. In addition, certain chemicals useful as processing aids may be incorporated into the finished product. Titanium dioxide may be used not only to add a white component of color, but also to serve as a sunscreen.

The lip cosmetic of the invention may also employ vitamins, minerals, antioxidants, drugs, organic compounds, herbs, proteins, currant extracts, root extracts, enzymes, sorbitol, pectin, and PCA to take advantage of their known coloring, flavoring, moistening, and adhering properties.

The invention may be further illustrated by way of the following examples.

EXAMPLE 1

The first step in formulating the lip cosmetic of the preferred embodiment of the invention is to create the sealer. The sealer is formed by mixing the film-forming agent in the organic solvent. Specifically, 3.6 percent by weight of AMPHOMER LV-71, obtained from National Starch and Chemical Company, and 2.7 parts by weight Ethocel N-4, obtained from Aqualon Corporation, are mixed at room temperature in 93.7 parts 190-proof specially denatured alcohol, sold as SDA 40B-190. The Ethocel N-4 provides ethyl cellulose which functions as an adjunct film former in the sealant. The sealer is then momentarily set aside.

Five parts by weight of a dispersion of D&C Red No. 7 in castor oil and 0.5 parts by weight of a dispersion of D&C Orange No. 5 in castor oil are then selected for use as the pigment or coloring agent. Both the D&C Red No. 7 and the D&C Orange No. 5 are obtained commercially "ground" in a castor oil base. The composition of these pigments is like a plastic material. Both the D&C Red No. 7 and the D&C Orange No. 5 each comprise about fifty percent of the total weight of their respective dispersions. The remaining weight of the dispersions is attributable to the castor oil. The pigments should be obtained in as finely ground a form as possible. The pigment dispersions are mixed together along with another 0.5 parts by weight castor oil.

The pigment and castor oil mixture is then mixed in with the sealer, also at room temperature. The AMPHOMER, the Ethocel, and the pigment ingredients are all readily soluble in the denatured alcohol. When mixed the formulation forms a somewhat turbid solution. Pigment grinds can be stirred into the sealer in any convenient manner. The resultant liquid mixture is one preferred embodiment of a cosmetic according to the invention.

EXAMPLE 2

The formulation of Example 1 is repeated but with the addition of two parts methyl silicone to the sealer prior to adding the pigments to the sealer. The use of a dimethicone such as methyl silicone increases the shininess of the lip cosmetic.

EXAMPLE 3

The formulation of Example 1 is repeated but with the addition of two parts by weight of glycerin as a humectant in producing the sealer. The use of a humectant aids in moisturizing the lips.

EXAMPLE 4

A sealer is first prepared by mixing 4.3 parts by weight of AMPHOMER LV-71 along with 3.2 parts by weight Ethocell N-4 into 92.5 parts specially denatured alcohol SDA 40B-190. 8.25 parts of D&C Red No. 7 pigment dispersion in castor oil along with 0.25 parts D&C Orange No. 5 pigment dispersion in castor oil are then mixed with an additional 0.5 parts castor oil and introduced into the quantity of sealer previously prepared. The sealer therefore constitutes 90.75 parts by weight of the total composition. The pigment grinds and additional castor oil are stirred into the sealer to produce the finished liquid lip cosmetic composition according to the invention.

All of the formulations of the lip cosmetic of the foregoing examples will dry in a thin film, when applied to the lips. The lip cosmetic will not crack or cake even with repeated applications. When any of the foregoing formulations are applied to a wearer's lips in at least three layers, the lip cosmetic covering provided will last a wearer engaged in virtually any normal activity throughout an entire day without fading or rubbing off.

Undoubtedly, numerous variations and modifications of the invention will become readily apparent to those familiar with cosmetic products. Accordingly, the scope of the invention should not be construed as limited to the specific examples described, as those examples are presented herein only as being illustrative of the many formulations possible according to the invention.

We claim:

1. A lip cosmetic comprising from about one to about ten parts ethyl cellulose, from about one to about ten parts of a cosmetic pigment, from about 70 to about 95 parts of an organic solvent, from about one to about ten parts of copolymers of N-tert-octylacrylamide, methyl methacrylate, hydroxypropyl methacrylate, acrylic acid and/or t-butyl aminoethyl methacrylate, and castor oil.

2. The lip cosmetic of claim 1 wherein said copolmyer resin is an octylacrylamide/acrylate/butylaminoethylmethacrylate copolymer.

3. The lip cosmetic of claim 2 wherein said copolymer is octylacrylamide/acrylate/butylaminoethylmethacrylate copolymer.

4. A lip cosmetic comprising from about one to about ten parts ethyl cellulose, from about one to about ten parts of a cosmetic pigment, from about 70 to about 95 parts of an organic solvent, from about one to about ten parts of an alcohol soluble and water insoluble resin selected from the group consisting of octylacrylamide copolymers, acrylate copolymers, butaminoethyl methacrylate copolymers, and polyvinyl acetate copolymers, and further comprising castor oil.

5. The lip cosmetic of claim 4 additionally comprising at least one part of a humectant, an ultraviolet screening agent or a dimethicone, or a combination thereof.

6. The lip cosmetic of claim 4 wherein said organic solvent is ethyl alcohol.

7. The lip cosmetic of claim 1 comprising from about four to about six parts copolymer resin, from about three to about four parts ethyl cellulose, from about seven to about nine parts of said pigment, and from about eighty to about eighty five parts of said organic solvent.

* * * * *